United States Patent [19]

Edelson

[11] Patent Number: 5,383,847
[45] Date of Patent: Jan. 24, 1995

[54] NON-SPECIFIC IMMUNE SYSTEM ENHANCEMENT

[75] Inventor: Richard L. Edelson, Westport, Conn.

[73] Assignee: Therakos, Inc., West Chester, Pa.

[21] Appl. No.: 921,865

[22] Filed: Jul. 29, 1992

Related U.S. Application Data

[63] Continuation-in-part of Ser. No. 502,083, Mar. 29, 1990, Pat. No. 5,147,289.

[51] Int. Cl.$^6$ ............................................. A61M 37/00
[52] U.S. Cl. .............................................. 604/6; 604/4
[58] Field of Search .................. 604/4, 5, 6, 20, 19, 604/27, 28

[56] References Cited

U.S. PATENT DOCUMENTS

| | | | |
|---|---|---|---|
| 4,398,906 | 8/1983 | Edelson | 604/6 |
| 4,428,744 | 1/1984 | Edelson | 604/6 |
| 4,464,166 | 8/1984 | Edelson | 604/6 |
| 4,568,328 | 2/1986 | King | 604/6 |
| 4,613,322 | 9/1986 | Edelson | 604/6 |
| 4,683,889 | 8/1987 | Edelson | 604/6 X |
| 4,708,715 | 11/1987 | Troutner et al. | 604/6 |
| 4,915,683 | 4/1990 | Sieber | 604/4 |

Primary Examiner—Sam Rimell
Attorney, Agent, or Firm—Richard J. Grochala

[57] ABSTRACT

The present invention pertains to a method for non-specifically enhancing the immune system response of a mammal to an antigen which comprises the steps of (a) withdrawing leukocyte containing material from the mammal, (b) treating the withdrawn leukocytes in a manner to alter the cells, and (c) returning the treated leukocytes to the mammal. In one embodiment, the method for non-specifically enhancing the immune system response of a mammal is carried out in conjunction with artificially contacting the mammal's immune system with an antigen for a suitable period of time to stimulate the immune system. In another embodiment, the mammal's immune system is naturally exposed to the antigen prior to the non-specific enhancement of the immune system. In yet another embodiment, the invention is directed at a method for preparing an autologous non-specific leukocyte adjuvant.

4 Claims, No Drawings

NON-SPECIFIC IMMUNE SYSTEM ENHANCEMENT

This application is a continuation-in-part of U.S. Ser. No. 502,083, filed Mar. 29, 1990, now U.S. Pat. No. 5,147,289.

BACKGROUND OF THE INVENTION

1. Field of the Invention

The present invention pertains to methods for non-specifically enhancing the immune system response of a subject. In one embodiment, the immune response is enhanced in conjunction with the artificial contact of the immune system of the subject with an antigen. In another embodiment, the vigor of a weak but existing immune response is enhanced. Specifically, the method comprises withdrawing leukocytes from a subject, physically altering the withdrawn leukocytes, and returning the altered leukocytes to the subject to enhance the immune response.

2. Description of the Prior Art

Immune system responses may be classified as humoral responses or cell-mediated responses. A humoral response is a response which is mediated by B lymphocytes in the form of freely diffusible antibody molecules. A cell-mediated response is a response mediated by specifically reactive lymphocytes, such as T lymphocytes or T cells, rather than antibodies.

Basic differences exist between humoral responses and cell-mediated responses. The time period from exposure to an antigen until elicitation of an immune reaction is minutes to hours for a humoral response and one or more days for a cell-mediated response. Humoral antibodies are generally specific for small antigenic determinants.

T lymphocytes are generally specific for antigens associated with specific molecules on cell surfaces.

Millions of distinct T cell clones exist in a particular person. Each clone is characterized by the proteins (the T cell receptor) carried on the surface of the T cell. The interaction of a receptor with a particular antigen requires that the receptor have a receptor site which is geometrically and chemically receptive to a corresponding site on the antigen. The forces which bind a receptor to an antigen consist of attractive forces which include hydrogen bonding, nonpolar bonding, ionic interactions, and Van der Waal's forces. The strength of these forces is inversely proportional to the distance between the interacting groups. Any structural variations in the geometry of the antigen can inhibit or prevent the binding of the receptor to the antigen. Once a receptor binds to an antigen on a cell, the cell may become activated, produce immunologically important molecules, divide to form many identical cell copies, and generally produce a strong and specific immunological reaction.

T cell reactions or cell-mediated responses are generally a beneficial defense of the body. A deficiency in the immune system response (immunodeficiency disease) leads to attack by pathogens, viruses, bacteria and fungi or cancer. Certain cell-mediated responses, however, are harmful because they cause tissue destruction. Examples of such harmful immune responses are hypersensitivity reactions (delayed-type and immediate), rejections of allografts, graft-versus-host reactions, and some allergic reactions. In addition, some autoimmune diseases are also harmful, such as myasthenia gravis, rheumatoid arthritis, systemic lupus erythematosus, multiple sclerosis, some forms of diabetes mellitus, thyroiditis, anterior uveitis, and Grave's disease.

One such harmful cell-mediated response is the rejection of allografts. An allograft (allogeneic graft, homograft) is a graft of a cell, tissue or organ which is transferred from a donor to a recipient of the same species but of disparate genotype. Because of extensive polymorphism of certain surface glycoproteins (glycoproteins existing in different forms at different stages of development), the grafted cells almost always have on their surfaces histocompatibility or transplantation antigens that are lacking on host cells and vice versa. The host responds by rejecting the allograft through a cell-mediated response.

A graft-versus-host reaction (GVH) occurs when lymphocytes are transferred from an immunologically competent donor (e.g., normal adult) to an allogeneic incompetent recipient (e.g., newborn). Ordinarily an immunologically competent host will destroy an allograft through a cell-mediated response. However an incompetent host cannot reject such a graft and the graft instead rejects the host. These reactions have clinical importance when normal thymus or bone marrow cells are transferred to immunodeficient humans (e.g., infants with genetic defects, subjects with leukemia treated with cytotoxic drugs and/or whole-body x-irradiation).

In autoimmune diseases, the immune system fails to recognize certain cells or parts of cells as its own ("self"). Autoimmunity is characterized by a specific humoral or cell-mediated response against the constituents of the body's own tissues (autoantigens) resulting in tissue destruction. This autoimmune response is characterized by the production of autoantibodies and autoreactive T cells.

Allergies are a hypersensitive state caused by exposure of the immune system to a particular allergen, and re-exposure, which causes an altered capacity to react. Allergic responses may be immediate or delayed. In some allergic responses, the immune system responds to a normally harmless substance, such as pollen, animal dander, or dust. In these allergic responses, sensitized T lymphocytes react with an allergen or antigen and release lymphokines which produce inflammation. Disease results from the inflammatory reaction caused by these environmental antigens. An example of such an allergic reaction is allergic contact dermatitis.

U.S. Pat. Nos. 4,321,919, 4,398,906, 4,428,744, and 4,464,166, all issued to Edelson, the contents of which are incorporated herein by reference, describe methods for specifically reducing the functioning lymphocyte population of a human subject. The Edelson references describe methods for treating the blood of a diseased subject wherein the disease-producing blood cells have been naturally stimulated as a consequence of the disease state. Specifically, the methods involve treating such naturally stimulated specific human blood cells, such as lymphocytes, with a dissolved photoactivatable drug, such as a psoralen, which is capable of forming photoadducts with the DNA in the cells in the presence of ultraviolet radiation. The lymphocytes and photoactivatable drug are then treated extracorporeally with ultraviolet radiation thereby modifying the lymphocytes. Following extracorporeal irradiation, the modified specific lymphocytes are returned to the subject. The modified specific lymphocytes are cleared from the subject's system by natural processes, but at an accelerated pace, presumably because of disruption of cell membrane integrity, alteration of the DNA within the cells, or similar conditions, often associated with substantial loss of cellular effectiveness or viability.

European Patent Application publication number 284,409, published Sep. 28, 1988, (U.S. Pat. No. 4,838,852), issued to Edelson et al., the contents of which are incorporated herein by reference, describes a method for specifically altering the immune system response of a subject to a specific antigen. Specifically, the Edelson et al. method comprises the steps of (a) contacting the subject's immune system with the specific antigen for a suitable time to artificially stimulate the immune system, (b) withdrawing blood cell containing material, including antigen stimulated blood cell material, from the subject, (c) treating the withdrawn material or cells so as to alter the specifically stimulated cells, and (d) returning the treated material or cells to the subject. Edelson et al. states that it may be possible to alter the cells and render them incapable of recognizing an antigen by first withdrawing blood cell containing material from the subject, treating the withdrawn material to alter the cells, returning the treated material to the subject and then contacting the subject's immune system with a specific antigen.

European Patent Application publication no. 333,606c, published Sep. 20, 1989, discloses a method for treating an autoimmune disease which comprises activating T lymphocyte cells specific for the autoimmune disease by the steps of exposing the T cells to an antigen specific for the autoimmune disease and treating the cells with a photoreactive psoralen cross-linking agent selective for the receptor on the cell membrane followed by photoactivation.

Specific immune unresponsiveness has been reported to be induced in vivo in rodents by immunizing the animal with autologous antigen-specific lymphoblasts obtained after in vitro sensitization, fractionation, and emulsification in Freund's complete adjuvant, L. C. Andersson et al., *Nature*, 264, pp. 778–780 (1976). Use of the nonspecific adjuvant to stimulate the specific response was necessary in that study.

Pretreatment of effector cells with 8-methoxypsoralen and ultraviolet A light has been reported to render the specific effector cells of graft rejection immunogenic for the syngeneic recipient, M. Perez et al., *The Journal of Investigative Dermatology*, 92, pp. 669–676 (1989). Reinfusion of photodamaged cells results in an immunosuppressive host response that permits prolonged retention of histoincompatible skin grafts and specifically inhibits in vitro and in vivo responses that correlate with allograft rejection.

Thus, a variety of methods are known to disable specific lymphocytes in diseased subjects, to attenuate specific lymphocytes to create vaccines, and to disable specific artificially-stimulated lymphocytes in healthy subjects to prevent disease. There is still a need, however, for a method to non-specifically enhance the immune system response of a subject. Such a method would permit the stimulation of a competent or incompetent immune system prior to an anticipated natural or artificial contact with an antigen, would permit the stimulation of an immune system in a subject already naturally but weakly stimulated with an antigen such as those associated with immunodeficiency disease and chronic infections, and would permit the stimulation of an immune system in a subject about to receive a vaccine. Also, immunoregulatory T cells capable of inhibiting undesirable immunologic reactions such as those found in autoimmune diseases or graft rejections could also be stimulated and weak anti-tumor responses could be enhanced. The present invention provides such a method for non-specifically enhancing the immune system response of a subject optionally with or without artificially contacting the subject's immune system with an antigen. The present invention also provides a method for preparing an autologous non-specific leukocyte adjuvant.

SUMMARY OF THE INVENTION

The present invention pertains to a method for non-specifically enhancing the immune system response of a mammal which comprises the steps of (a) withdrawing leukocyte containing material from the mammal, (b) treating the withdrawn leukocytes in a manner to alter the cells, and (c) returning the treated leukocytes to the mammal. In one embodiment, the method for non-specifically enhancing the immune system response of a mammal is carried out in conjunction with the artificial contact of the mammal's immune system with an antigen for a suitable period of time to stimulate the immune In another embodiment, the mammal's immune system is naturally exposed to the antigen prior to the non-specific enhancement of the immune system. In yet another embodiment, the invention is directed at a method for preparing an autologous non-specific leukocyte adjuvant.

DETAILED DESCRIPTION OF THE INVENTION

In one embodiment, the present invention pertains to a method for non-specifically enhancing the immune system response of a mammal which comprises the steps of (a) withdrawing leukocyte containing material from the mammal, (b) treating the withdrawn leukocytes in a manner to alter the cells, and (c) returning the treated leukocytes to the mammal.

In another embodiment, the invention pertains to a method for non-specifically enhancing the immune system response of a mammal to an antigen which comprises the steps of (A) enhancing the immune system response by (a) withdrawing leukocyte containing material from the mammal, (b) treating the withdrawn leukocytes in a manner to alter the cells, (c) returning the treated leukocytes to the mammal, and (B) artificially contacting the mammal's immune system with the antigen for a suitable period of time to stimulate the immune system. In one example, the method for enhancing the immune response is carried out before the subject's immune system is artificially contacted with the antigen. In another example, the method for enhancing the immune response is carried out simultaneously with the artificial or natural contacting of the subject's immune system with the antigen.

In yet another embodiment, the invention pertains to a method for preparing an autologous non-specific leukocyte adjuvant. Some antigens against which an immunologic reaction would be desirable are naturally occurring. These naturally occurring antigens include those found on malignant cells and on undesirable disease causing T cell clones. In the case of progressing disease, immunologic reactions against these disease causing cells may exist but are clearly too weak to halt the progression of the disease. The autologous non-specific leukocyte adjuvants of the present invention would enhance these weak immunologic reactions and permit disease control.

As used herein, the term "artificially stimulate" or "artificially contact" refers to the positive step of contacting and stimulating the immune system of a subject with an antigen through human intervention. The term "naturally stimulate" or "naturally contact" refers to the contacting and stimulating of the immune system of a subject with an antigen, without human intervention, as a natural consequence of disease. The subject (patient, host) to be treated in the present invention is a mammal, preferably a human.

Adjuvants are substances that when mixed with an antigen enhance antigenicity and give a superior immune response. For example, Freund's incomplete adjuvant is a water-in-oil emulsion which contains an antigen in an aqueous phase suspended in a light-weight paraffin oil with the aid of an emulsifying agent. On injection, this mixture induces strong persistent antibody formation. Freund's complete adjuvant, which contains killed, dried mycobacteria, e.g., *Mycobacterium butyricum*, in the oil phase, elicits cell-mediated immunity (delayed hypersensitivity) as well as humoral antibody formation. Because of toxicity reasons, adjuvants such as Freund's adjuvant cannot be used in humans.

Applicant has found that reinfusion of damaged nonspecific leukocytes to a subject enhances the capacity of that subject to manifest an immunologic response to specific antigens simultaneously presented to the subject. While not wishing to be bound by theoretical considerations, applicant believes that, in contrast to the reinfusion of damaged specific pathogenic leukocytes, the reinfusion of damaged nonspecific nonpathogenic leukocytes to a subject does not generally prompt an immunologic response against the nonspecific leukocytes in the subject. Rather, such reinfusion prompts a heightened state of awareness in the immune system which results in an general enhancement in the immune response. Applicant believes that the damaged nonspecific nonpathogenic leukocytes act as an autologous non-specific leukocyte adjuvant.

The reinfusion of damaged pathogenic T cells, belonging to an expanded clone, leads to a specific immunological reaction against these T cells presumably because the immune system readily responds to the large number of identical T cells. The reinfusion of damaged nonpathogenic T cells, which do not belong to an expanded clone, does not lead to an immunological reaction presumably because the immune system does not respond to smaller numbers of cells belonging to each of the very large number of different T cells clones. Because these damaged nonpathogenic T cells must nevertheless be cleared from the subject, the immune system responds by raising the level of the immune response to an excited or an enhanced level.

In the method of the present invention, leukocyte containing material is withdrawn from a subject. Leukocytes are white blood cells which include lymphocytes, polymorphonuclear cells and monocytes. In a preferred embodiment, the leukocytes are lymphocytes which include T cells and B cells. In a more preferred embodiment, the lymphocytes are T cells.

In a preferred embodiment, the leukocyte containing material is selected from the group consisting of blood, lymph fluid, bone marrow, lymphatic organ tissue, and any other body fluid or tissue which contains leukocytes. Lymphocytes circulate through the lymph fluid and tissue spaces and aggregate in the primary and secondary lymphatic structures, such as the thymus, spleen and lymph nodes. Hence, lymphocytes may be obtained from the lymph fluid or the primary or secondary lymphatic structures, or even from infiltrated organ such as skin. In a more preferred embodiment, the leukocyte containing material is blood which contains large amounts of lymphocytes. Withdrawal of blood and reinfusion of treated blood to a subject is simple and convenient. Such methods are well known in the art and are analogous to methods used in blood dialysis.

In accordance with this invention, the leukocytes withdrawn from a subject are treated to alter them, e.g., to lethally damage, functionally inactivate, or physically alter the structure of the cell membranes or protein components. Preferably, such inactivation treatment disrupts the membrane integrity of the withdrawn leukocytes, and more preferably such treatment chemically alters the cells, such as altering the DNA or the cytoplasmic proteins of the leukocytes, so as to make them immunostimulatory. Such inactivation treatment may be accomplished by several means and is within the capabilities of those skilled in the art without the need for undue experimentation. For example, leukocytes may be inactivated by exposure of the leukocytes to ultraviolet radiation in the presence of a photoactivatable agent (photopheresis), by exposure to high or low temperature, to high or low pH values, to high or low pressure, to hypotonic solutions, to chemotherapeutic agents such as mitomycin C, to ultraviolet light without a photoactivatable agent, to visible light with a photoactivatable agent such as hematoporphyrin, to monoclonal antibodies, to toxins such as ricin, or by passage of the leukocytes through resinous materials. In some cases, mere handling of the leukocytes will accomplish the desired inactivation treatment. Preferably, the leukocytes are gently damaged by ultraviolet radiation in the presence of a photoactivatable agent.

The photopheresis method of treating leukocytes involves withdrawing of the leukocytes, forming the withdrawn leukocytes into an extracorporeal stream, flowing the stream through a treatment chamber substantially transparent to ultraviolet radiation, irradiating the stream in the chamber with ultraviolet radiation in the presence of the photoactivatable agent and returning the blood to the subject. In this method, blood, or leukocyte cells derived from blood, are contacted with a photoactivatable agent which is dissolved in the blood by mixing the photoactivatable agent with the blood either (a) by administering the photoactivatable agent orally to the subject prior to withdrawing the blood, or (b) by mixing the photoactivatable agent with the blood subsequent to withdrawing the blood from the subject.

The photoactivatable agent may be any agent which has an affinity for an important component of the nucleated leukocytes, such as the nucleic acid and when activated by ultraviolet radiation, is capable of seriously injuring the cells, such as cross-linking DNA to chemically bond the photoactivatable agent with the nucleic acid. Examples of photoactivatable agents are psoralens, photoactivated cortisone, photoactivated antibodies specifically reactive to malignant lymphocytes and photoactive antibodies specifically receptive to the undesirable antibodies of a subject. Other photoactivatable agents include photoactive pyrene and monoclonal antibodies which have been linked to porphyrin molecules. A preferred class of photoactivatable agents is the psoralens. Preferred psoralens include 8-methoxypsoralen (8-MOP) and aminomethyltrimethyl-psoralen (AMT).

The photoactivatable agent 8-methoxypsoralen occurs naturally in a variety of plants, including limes, parsley and figs and in its inactive form (not photoactivated) is non-toxic to humans at pharmacologic doses. The photoactivatable agent 8-methoxypsoralen is a preferred agent to treat lymphocytes because it may be transformed from a biologically inert state by low energy ultraviolet A radiation to a transiently excited state capable of covalently cross-linking DNA and other macromolecules. Ultraviolet A radiation, which passes through clear glass and some translucent plastics, activates 8-methoxypsoralen to an active form which cross-links sister strands of DNA by forming bifunctional adducts with pyrimidine bases, thereby transforming the molecule into a potent chemotherapeutic agent. Since the half life of the photoactivated 8-methoxypsoralen is only in the microsecond range, tissues not simultaneously exposed to both the drug and ultraviolet A radiation are spared the toxic effects of the active form.

Since only oral preparations of 8-methoxypsoralen are available for clinical use, the appropriate concentration of the photoactivatable agent (about 0.6 mg per kg of body weight of 8-methoxypsoralen) must be orally administered to the subject prior to the time of photopheresis treatment (about one to two hours). Blood is then withdrawn from the subject during the photopheresis procedure. The preferred psoralen concentration in the blood is from about 1 nanogram to about 1000 micrograms per milliliter of blood. Alternatively, a known quantity of psoralen could be administered.

In a preferred embodiment, the flow rate of the extracorporeal blood stream is in the range from about 10 ml/min to about 75 ml/min. Preferably, the blood stream should be irradiated with photoenergy in the ultraviolet wavelength range (UVA, UVB, UVC). Preferably ultraviolet A will be used to effectively deliver from about 0.1 joules/cm$^2$ to about 100 joules/cm$^2$ to the actual leukocytes. More preferably, the radiation dose level of the blood is from about 5 joules/cm$^2$ to about 60 joules/cm$^2$ to the leukocytes. The optimal ultraviolet wavelength range for irradiating leukocytes in the presence of 8-methoxypsoralen is from about 320 nm to about 400 nm, preferably from about 334 nm to about 346 nm. The leukocytes may be exposed to ultraviolet radiation for a period from about 5 minutes to about 6 hours. Within the optimal wavelength range, an approximately 270 minute exposure to ultraviolet A is required to provide the average leukocyte with 2 joules/cm$^2$ of leukocyte.

The photopheresis method may be carried out in a single apparatus which comprises a continuous centrifuge for separating leukocytes, i.e. white blood cells, from the blood withdrawn from the subject. The centrifuge may be used in an initial discontinuous leukapheresis step, wherein leukocytes are separated from the blood in one or more cycles. This may be accomplished by having the subject recline in a bed and then leukapheresing heparinized blood during 6 cycles through a continuously spinning centrifuge bowl, permitting removal of a total of about 240 ml of leukocyte enriched blood. This blood may then be pooled with about 300 ml of plasma obtained during the same procedure from the subject (removed 2 hours following ingestion of 0.6 mg per kg of body weight of 8-methoxypsoralen) and 200 ml of sterile normal saline, yielding a final hematocrit of approximately 6.4 plus or minus 1.7% and containing from about 10% to about 50% of the number of lymphocytes in the subject's blood at the initiation of the leukapheresis. The total volume may then be passed through a disposable sterile irradiation chamber in order to expose it to (ultraviolet A) energy. The chamber may be in the form of a six-chambered disposable cassette.

Each chamber of the cassette may be composed of an outer polycarbonate sheath opaque to ultraviolet A and an inner ultraviolet A transparent acrylic tube surrounding a fluorescent ultraviolet A radiation source. These two walls, between which the blood is pumped, are approximately 1.0 mm apart. Flow in each chamber is from bottom to top, with shunts connecting the top of each chamber to the bottom of the next chamber. Total volume of the cassette is abut 190 ml. Incorporated into this ultraviolet A exposure system may be an automatically reversible blood pump to permit continuous recycling of the blood through the cassette and temperature sensors to ensure that the blood is not heated above 41° C. Following exposure of blood to ultraviolet A, the entire volume is returned to the subject.

The withdrawing of the leukocytes, passage of the leukocytes to the treatment station and return of the blood to the subject may be handled in batch form but preferably is carried out as one continuous operation. In a preferred embodiment, the continuous operation comprises forming the withdrawn material or leukocytes into an extracorporeal stream, (b) flowing the stream through a treatment chamber substantially transparent to ultraviolet radiation, and (c) irradiating the stream in the chamber with ultraviolet radiation in the presence of the photoactivatable agent.

Methods and apparatus useful for irradiating blood are described in detail in U.S. Pat. Nos. 4,573,960, 4,568,328, 4,578,056, and 4,428,744, the contents of which are incorporated herein by reference. Additional methods and apparatus for irradiating blood are described in co-pending, commonly assigned U.S. patent application Ser. No. 834,292 entitled "Concurrent On-Line Irradiation Treatment Process", and U.S. patent application Ser. No. 834,258 entitled "Irradiation Chamber for Photoactivation Patient Treatment system," the contents of which are incorporated herein by reference.

In a specific embodiment, the present invention provides a method for enhancing the immune system response of a mammal. In another specific embodiment, the present invention provides a method for preparing an autoiogous non-specific leukocyte adjuvant. The method comprises the following steps:

(a) withdrawing leukocyte containing material from the mammal, (b) treating the withdrawn leukocytes in a manner to alter the cells, and (c) returning the treated leukocytes to the mammal.

In yet another specific embodiment, the present invention is directed at an autologous non-specific leukocyte adjuvant prepared by the method which comprises the steps of:

(a) withdrawing leukocyte containing material from the mammal, (b) treating the withdrawn leukocytes in a manner to alter the cells, and (c) returning the treated leukocytes to the mammal.

In one example of the present invention, the immune response of a subject is enhanced prior to an anticipated natural contact of the subject with an antigen. In another example, the immune response of a subject is enhanced after the subject has already been naturally contacted with an antigen and has manifested the associated disease.

The present invention also pertains to methods for non-specifically enhancing the immune system response of a subject in conjunction with the artificial contacting of the subject's immune system with an antigen. In one example, the immune response is enhanced before the subject's immune system is artificially contacted with the antigen. In another example, the immune response is enhanced simultaneously with the artificial contacting of the subject's immune system with the antigen.

In general, any antigen to which the immune system response is to be enhanced may be used including those antigens associated with a disorder, pathological condition or disease state. Especially useful antigens include those associated with a disorder caused by a deficiency of the immune system such as an immunodeficiency disease. In a preferred embodiment, the antigen is in the form of a vaccine.

The specific antigen of interest may serve to stimulate a T cell expressing unique T cell receptors which are capable of serving as clonotypic antigens. In such a case, clonal expansion of these circulating aberrant T cells mediates the disorder sought to be controlled. The present invention provides a method for enhancing a clone-specific immune reaction which limits the activity of such an aberrant population of T cells.

Exemplary immunodeficiency diseases include acquired immunodeficiency syndrome (AIDS), certain forms of cancer, immunodeficiency of old age, and immunodeficiency following immunosuppressive therapy. Exemplary hypersensitivity diseases include delayed-type hypersensitivity reaction, autoimmune disease, allergy, infectious disease, rejection of allografts, and graft-versus-host reaction.

The artificial contacting of the subject's immune system with the specific antigen may be achieved in any manner which introduces the antigen into the subject's immune system, e.g. by injection directly into the blood stream, the lymphatic system, the lymphoid organs, or the skin. The antigen is then permitted to be in contact with, or exposed to, the subject's immune system, for a suitable time period so as to permit stimulation of certain leukocytes specifically in response to that antigen. This suitable period of time could be as long as one year but in most instances is shorter and generally is no longer than 72 hours.

In a specific embodiment, the present invention provides a method for enhancing the immune system response of a mammal to an antigen. In another specific embodiment, the present invention provides a method for preparing an autologous non-specific leukocyte adjuvant to an antigen. The method comprises the following steps:

(A) enhancing the immune system response by:
(a) withdrawing leukocyte containing material from the mammal,
(b) treating the withdrawn leukocytes in a manner to alter the cells,
(c) returning the treated leukocytes to the mammal, and (B) artificially contacting the mammal's immune system with the antigen for a suitable period of time to stimulate the immune system.

In yet another specific embodiment, the present invention provides an autologous non-specific leukocyte adjuvant to an antigen prepared by the method which comprises the steps of:

(A) enhancing the immune system response by:
(a) withdrawing leukocyte containing material from the mammal,
(b) treating the withdrawn leukocytes in a manner to alter the cells,
(c) returning the treated leukocytes to the mammal, and (B) artificially contacting the mammal's immune system with the antigen for a suitable period of time to stimulate the immune system.

In one example of the present invention, the immune response of a subject is enhanced before the subject is artificially contacted with an antigen, such as when the antigen is in the form of a vaccine. In another example, the immune response of a subject is enhanced after the subject has already been naturally contacted with an antigen but before the subject is artificially contacted with the same or a different antigen.

When the immune system of a subject is enhanced without artificially contacting the immune system with an antigen, the method of the present invention may be used prophylactically or therapeutically. For example, the method may be used prophylactically when the immune response of a subject is enhanced prior to an anticipated natural contact of the system with an antigen. Hence, the competent or incompetent immune system of a subject may be enhanced to increase the vigor of the immune system response before the subject is naturally contacted with an antigen.

The method of the present invention may also be used therapeutically such as when the immune response of a subject is enhanced after the subject has already been naturally contacted by an antigen. For example, the method can be used to increase the vigor of the immune system response of a subject who has chronic infections, an immunodeficiency disease, a cancer, or an auto immune disease.

When the method of the present invention is used to enhance the immune response of a subject who has an immunodeficiency disease such as acquired immunodeficiency syndrome (AIDS) or certain forms of cancer, the method may be used to invigorate an incompetent immune system. While the immune system of the subject has not effectively attacked the antigen associated with the immunodeficiency disease prior to immune system enhancement, the method of the present invention may be used to enhance the immune response of the subject so as to induce an immunological attack on the antigen which previously was not effectively attacked. Similarly, the present method can be used to enhance the response of an incompetent immune system of a subject who is susceptible to chronic infections.

When the method of the present invention is used to enhance the immune response of a subject who has a hypersensitivity disease or autoimmune disorder, the method may be used to correct a deficiency or imbalance in the immune system. Hypersensitivity and autoimmune disorders are believed caused by aberrant T cells which are not being controlled by corresponding suppressor cells. The method of the present invention may be used to alter the immune response of a subject so as to prompt the suppressor cells to mount an immunological attack on the aberrant T cells.

When the immune system of a subject is enhanced in conjunction with artificially contacting the immune system with an antigen, the method of the present invention may be used prophylactically or therapeutically. For example, the method may be used prophylactically when the immune response of a subject is enhanced before the subject is artificially contacted with an antigen. Hence, the immune system response of a subject may be enhanced to increase the vigor of the immune response prior to administering a vaccine to a subject to improve vaccine formation.

The method of the present invention may also be used therapeutically such as when the immune response of a subject is enhanced in conjunction with artificially contacting the immune system of a subject with an antigen, after the subject has already been naturally contacted by an antigen. Naturally stimulated subjects may also be artificially stimulated with the same or a different antigen by the methods of the present invention to achieve a therapeutic result. In such a method, it may be possible to artificially stimulate the subject according to the methods of the present invention in order to alter the immune system response of the subject and achieve a beneficial therapeutic effect.

In that particular embodiment when the present invention is used to enhance the immune response of a subject who has an immunodeficiency disease, it has been found that only those individuals who have a sufficient number of helper/inducer T cells in their peripheral blood are capable of responding to the present method. The minimum number of normal helper/inducer T cells required for a response to therapy is 150 per cubic milliliter of blood. This number is substantially smaller than the approximately 1000 per cubic milliliter found in the blood of normal immunocompetent individuals. Therefore, a further aspect of the present invention is to provide a method for non-specifically enhancing the immune system response of an immunodeficient mammal to an antigen which comprises first determining if the mammal's helper/inducer T cell count is at least 150 per cubic milliliter of blood. If so, then leukocyte containing material is withdrawn from the mammal, treated in a manner to alter the cells and then returned to the mammal. As used herein, "immunodeficient" means an abnormally low T cell count as a consequence of the loss of T cells, as occurs in inflammatory bowel disease; or destruction of T cells by cytotoxic drugs or ionizing radiation; or displacement of normal T cells by malignant cells, such as in multiple myeloma or chronic lymphocytic leukemia or cutaneous T cell lymphoma; or from infection of T cells, as in AIDS.

Methods for determining the number of helper/inducer T cells in a subject's blood are well known in the art and include any of those that are normally used to measure or count blood cells, such as flow cytometry methods or FACS.

The reason for the requirement of at least 150 helper/inducer T cells per cubic milliliter of blood is that the response to the treatment step, such as when photopheresis is used, requires significant immunocompetence. When diseased blood T cells are chemically altered by ultraviolet activated psoralen outside the body and then returned, an immunologic reaction against these cells is induced in the patient. If the number of residual normal helper/inducer T cells is too low to allow immunocompetence, the patient cannot respond immunologically.

Throughout this application, various publications have been referenced. The disclosures in these publications are incorporated herein by reference in order to more fully describe the state of the art.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

I claim:

1. A method for non-specifically enhancing the immune system response of an immunodeficient mammal to an antigen, the method comprising the steps of:
    a) determining if the mammal's helper/inducer T cell count is at least 150 per cubic milliliter of blood and, if so, conducting the following steps (b)–(d);
    b) withdrawing leukocyte containing material from the mammal;
    c) treating the withdrawn leukocytes in a manner to alter the cells; and
    d) returning the treated leukocytes to the mammal.
2. The method according to claim 1, wherein the mammal is a human.
3. The method according to claim 1, wherein the leukocyte containing material is selected from the group consisting of blood, lymph fluid, bone marrow, and lymphatic organ tissue.
4. The method according to claim 1, wherein the treatment of the leukocytes is by irradiating the leukocytes with ultraviolet radiation in the presence of a photoactivatable agent.

* * * * *